United States Patent
Wu (10) Patent No.: US 10,370,703 B2
(45) Date of Patent: Aug. 6, 2019

(54) METHOD FOR DETECTING GUANINE-ABASIC SITE IN DNA

(71) Applicant: NATIONAL INSTITUTE OF ADVANCED INDUSTRIAL SCIENCE AND TECHNOLOGY, Tokyo (JP)

(72) Inventor: Chun Wu, Ikeda (JP)

(73) Assignee: NATIONAL INSTITUTE OF ADVANCED INDUSTRIAL SCIENCE AND TECHNOLOGY, Tokyo (JP)

(*) Notice: Subject to any disclaimer, the term of this patent is extended or adjusted under 35 U.S.C. 154(b) by 189 days.

(21) Appl. No.: 15/126,178

(22) PCT Filed: Jan. 29, 2015

(86) PCT No.: PCT/JP2015/052475
§ 371 (c)(1),
(2) Date: Sep. 14, 2016

(87) PCT Pub. No.: WO2016/136999
PCT Pub. Date: Sep. 17, 2015

(65) Prior Publication Data
US 2017/0088884 A1    Mar. 30, 2017

(30) Foreign Application Priority Data
Mar. 14, 2014    (JP) .................................. 2014-052221

(51) Int. Cl.
| C12Q 1/68 | (2018.01) |
| C07H 21/00 | (2006.01) |
| C12Q 1/6827 | (2018.01) |
| C12Q 1/44 | (2006.01) |
| C12Q 1/6869 | (2018.01) |

(52) U.S. Cl.
CPC ............. *C12Q 1/6827* (2013.01); *C12Q 1/44* (2013.01); *C12Q 1/6869* (2013.01); *C12Y 301/21* (2013.01); *C12Y 301/21005* (2013.01)

(58) Field of Classification Search
CPC .................................. C12Q 1/68; C07H 21/00
See application file for complete search history.

(56) References Cited

U.S. PATENT DOCUMENTS

| 2004/0018526 A1* | 1/2004 | Hirose | ................. C12Q 1/6834 435/5 |
| 2006/0292611 A1 | 12/2006 | Berka et al. | |
| 2010/0216132 A1* | 8/2010 | Schwartz | ............ G01N 33/5308 435/6.14 |

FOREIGN PATENT DOCUMENTS

| JP | 2004-049182 A | 2/2004 |
| JP | 2006-172025 A | 6/2006 |
| JP | 2012-223203 A | 11/2012 |
| WO | WO 2009/082020 A1 | 7/2000 |

OTHER PUBLICATIONS

Biotrin OxyDNA Test : Instructions for use (Year: 2007).*
Buruskov et al., Biochemistry 64 :803 (Year: 1999).*
Cadet et al., Mutation Research 531:5 (Year: 2003).*
D izdaroglu et al. Free Radical Biology & Medicine32(11) :1102 (Year: 2002).*
Hirose et al. and Photobiology 76(2) : 123 (Year: 2002).*
Ide et al., Biochemistry 32 : 8276 (Year: 1993).*
Kow et al., Methods 22:164 (Year: 2000).*
Kubo et al., Biochemistry 31: 3703 (Year: 1992).*
Kurisu et al., Nucleic Acids Reseach Sup No. 45-46 (Year: 2001).*
Park et al., PNAS 89: 3375 (Year: 1992).*
Pierce Monomeric Avidin Kit (2011). https://assets.thermofisher.com/TFS-Assets/LSG/manuals/MAN0011221_Pierce_Monomeric_Avidin_UG.pdf (Year: 2011).*
Murata-Kamiya et al., Formation of 5-formyl-2'-deoxycytidine from 5-methyl-2'-deoxycytidine in duplex DNA by Fenton-type reactions and y-irradiation. Nucleic Acids Research 27 (22) : 4385 (Year: 1999).*
Wu et al., Biotinylation of Deoxyguanosine at the Abasic Site in Double-Stranded Oligodeoxynucleotides. Journal of Analytical Methods in Chemistry. Article ID 4681421 (4pgs) (Year: 2016).*
Yoshimoto et al., Fluorescence detection of guanine—adenine transition by a hydrogen bond forming small compound. Chem Commun. pp. 2960-2961 (Year: 2003).*
Bui et al., *Bioorganic Chemistry*, 30: 216-232 (2002).
Cortellino et al., *Cell*, 146: 67-79 (20011).
Ide et al., *Biochemistry*, 32: 8276-8283 (1993).
Olsen et al., *Chem. Res. Toxicol.*, 18: 730-739 (2005).
(Continued)

*Primary Examiner* — Ethan C Whisenant
(74) *Attorney, Agent, or Firm* — Leydig, Voit & Mayer, Ltd.

(57) ABSTRACT

The present invention provides a method for detecting the presence or absence of a guanine-abasic site, the method being a process for detecting guanine opposite at least one abasic sites generated in a double-stranded DNA, comprising:

(1) step 1 of site-selectively cleaving at least one abasic sites in a double-stranded DNA using an enzyme;
(2) step 2 of modifying the amino group at position 2 of guanine opposite the abasic sites using a modifier; and
(3) step 3 of performing polymerase chain reaction on the modified double-stranded DNA obtained by conducting step 1 and step 2, which serves as a template, to search for the presence or absence of an amplification product, the sequence of steps 1 and 2 being not limited to the order presented.

7 Claims, 6 Drawing Sheets
Specification includes a Sequence Listing.

(56) References Cited

OTHER PUBLICATIONS

Sato et al., *Analytical Sciences*, 29: 15-19 (2013).
Staehelin et al., *Biochimica et Biophysica Acta*, 31: 448-454 (1959).
Sun et al., *Analytical Chemistry*, 73(10): 2229-2232 (2001).
Japanese Patent Office, International Search Report in International Patent Application No. PCT/JP2015/052475 (dated Apr. 21, 2015).

\* cited by examiner

```
                              SEQUENCE LISTING

<160> NUMBER OF SEQ ID NOS: 7

<210> SEQ ID NO 1
<211> LENGTH: 100
<212> TYPE: DNA
<213> ORGANISM: Artificial Sequence
<220> FEATURE:
<223> OTHER INFORMATION: Synthetic 100 mer oligo DNA (20131226U)
<220> FEATURE:
<221> NAME/KEY: misc_feature
<222> LOCATION: (55)..(55)
<223> OTHER INFORMATION: n is dU (dideoxy uracil)

<400> SEQUENCE: 1
tgacttgcca cctatagaca gcccttgctc tcctgcagag tttggcaatg actcnggtca      60
ctgcatctgt gggacctggc tcagtctgcc aacttcactg                           100

<210> SEQ ID NO 2
<211> LENGTH: 100
<212> TYPE: DNA
<213> ORGANISM: Artificial Sequence
<220> FEATURE:
<223> OTHER INFORMATION: Synthetic 100mer oligo DNA (20131226G)

<400> SEQUENCE: 2
cagtgaagtt ggcagactga gccaggtccc acagatgcag tgaccggagt cattgccaaa      60
ctctgcagga gagcaagggc tgtctatagg tggcaagtca                           100

<210> SEQ ID NO 3
<211> LENGTH: 22
<212> TYPE: DNA
<213> ORGANISM: Artificial Sequence
<220> FEATURE:
<223> OTHER INFORMATION: Synthetic forward primer

<400> SEQUENCE: 3
cagtgaagtt ggcagactga gc                                               22

<210> SEQ ID NO 4
<211> LENGTH: 23
<212> TYPE: DNA
<213> ORGANISM: Artificial Sequence
<220> FEATURE:
<223> OTHER INFORMATION: Synthetic reverse primer

<400> SEQUENCE: 4
ctgacttgcc acctatagac agc                                              23

<210> SEQ ID NO 5
<211> LENGTH: 23
<212> TYPE: DNA
<213> ORGANISM: Artificial Sequence
<220> FEATURE:
<223> OTHER INFORMATION: Synthetic midreverse primer

<400> SEQUENCE: 5
ctgcagagtt tggcaatgac tcc                                              23

<210> SEQ ID NO 6
<211> LENGTH: 100
```

```
<212> TYPE: DNA
<213> ORGANISM: Artificial Sequence
<220> FEATURE:
<223> OTHER INFORMATION: Synthetic forward primer

<400> SEQUENCE: 6
cagtgaagtt ggcagactga gccaggtccc acagatgcag tgaccggagt cattgccaaa     60
ctctgcagga gagcaagggc tgtctatagg tggcaagtca                           100

<210> SEQ ID NO 7
<211> LENGTH: 99
<212> TYPE: DNA
<213> ORGANISM: Artificial Sequence
<220> FEATURE:
<223> OTHER INFORMATION: Synthetic reverse primer

<400> SEQUENCE: 7
tgacttgcca cctatagaca gcccttgctc tcctgcagag tttggcaatg actcggtcac     60
tgcatctgtg ggacctggct cagtctgcca acttcactg                            99
```

METHOD FOR DETECTING GUANINE-ABASIC SITE IN DNA

CROSS-REFERENCE TO RELATED APPLICATIONS

This patent application is the U.S. national phase of International Patent Application No. PCT/JP2015/052475, filed on Jan. 29, 2015, which claims the benefit of Japanese Patent Application No. 2014-052221, filed Mar. 14, 2014, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 2,180 bytes ASCII (Text) file named "726473ReplacementSequenceListing.txt" created Nov. 30, 2018.

TECHNICAL FIELD

The present invention relates to a method for detecting the presence or absence of a guanine-abasic site in DNA, a method for quantifying the guanine-abasic site, a method for detecting the position of a guanine-abasic site, and kits therefor.

BACKGROUND ART

Figure 1:
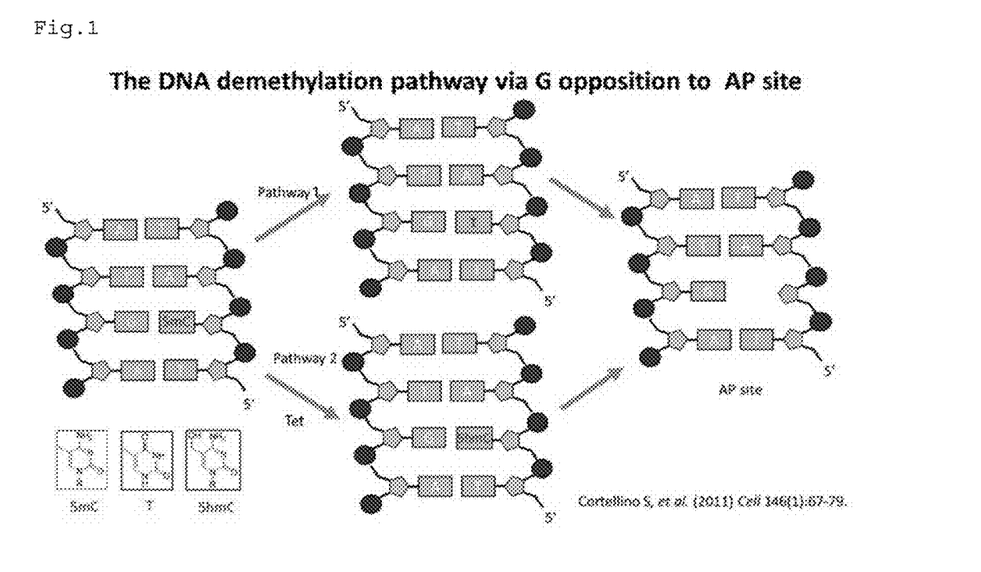
FIG. 1: DNA demethylation pathway involving the generation of a guanine-abasic site

In chromosome DNA of mammalian cells, cytosine in CpG islands composed of a CG dinucleotide sequence is known to be methylated or demethylated at its position 5. Methylation and demethylation of cytosine in CpG islands regulates the transcriptional regulation mechanism of genes. Typically, in the promoter region of a gene, a region containing many CpG islands is present, and the presence and absence of methylation of cytosine in the promoter region of a gene functions as an on-off switch for transcription of the gene. Although methylation of cytosine has long been studied, the details of cytosine demethylation have remained unknown for a long time. However, Non-patent Literature 1 has recently revealed that deamination of 5-methylcytosine or oxidation of 5-methylcytosine into 5-hydroxymethylcytosine causes the cytosine to protrude from the double helical structure, and thus causes the N-glycosidic site to undergo hydrolysis by an enzyme, thereby generating an abasic site (apyrimidinic site: AP site) opposite guanine (FIG. 1).

Figure 2:
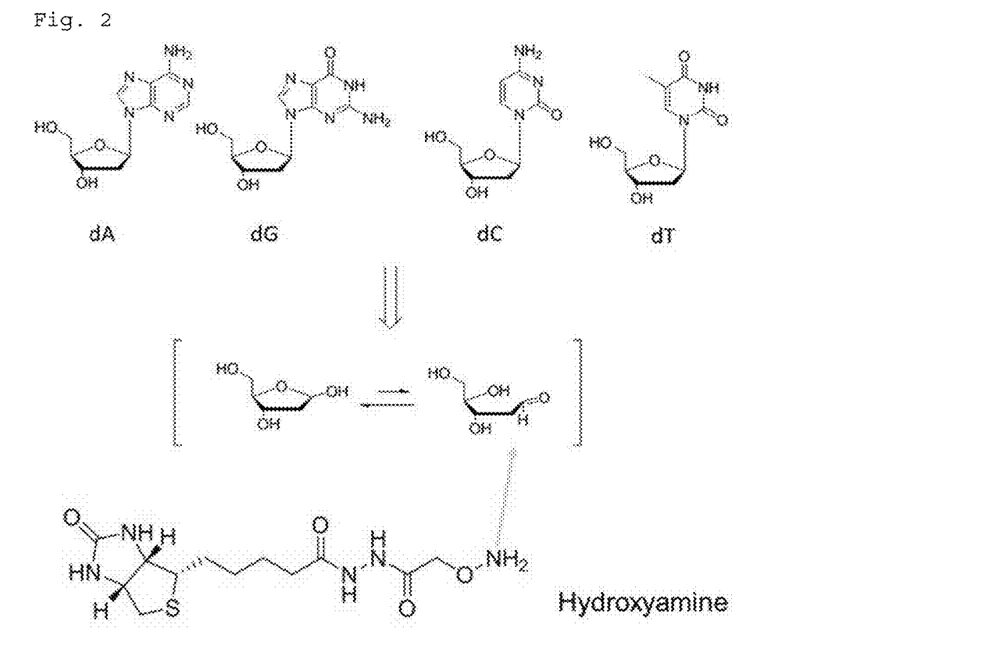
FIG. 2 shows the formation of the Schiff base by deoxyribose and hydroxylamine.

Cytosine demethylation is regulated by enzymes. However, the bases of the genomic DNA in mammalian cells are exposed to chemical substances, ultraviolet ray or X-ray irradiation, or oxidation stress, and 50,000 to 200,000 bases per day are eliminated at random, creating abasic sites. It is known that, as a result, a deoxyribose having an acetal structure generated by the elimination of any of four bases of DNA opens the ring by an equilibrium reaction and transforms into aldehyde (FIG. 2). Because the damage caused by the elimination of a base of DNA can be deeply involved in the transcription or translation of a gene, the analysis of the damage is important. At present, biotinylated hydroxylamine compounds disclosed in prior art (Non-patent Literature 2, Patent Literature 1) are commercially available. The reagents specifically bind to an abasic lesion and detect the coloration or luminescence caused by an enzyme using biotinylation and the specific bond with an avidin-enzyme conjugate. This detection technique is widely used, and exhibits high sensitivity and excellent quantification. However, the reagents are intended for measuring the average amount of abasic sites for the four bases of DNA, and cannot identify the position of the abasic sites in DNA or the type of corresponding bases in the complementary strand.

Formaldehyde, glyoxal, and a kethoxal compound, which is a derivative of glyoxal, have been long known to react with the amino group at position 2 of guanine in a single-stranded RNA or DNA (Non-patent Literature 3). In particular, glyoxal and its derivative, kethoxal, are known to react with guanine to form three ring structures. The reaction yield has recently been measured by mass spectrometry, which revealed that the reaction yield varies widely depending on the position of the guanine base in DNA, ranging from 9 to 89% (Non-patent Literature 4). However, even if 9 to 89% of guanine in a single-stranded DNA is modified, the DNA with 10% or more of unreacted guanine would sufficiently serve as a template for polymerase chain reaction, having little influence on PCR, which amplifies the DNA fragment by 2 to the power of n.

Endonucleases, which act on their substrate, abasic sites of DNA, are classified into two types: endonuclease IV and APEI nuclease, which are derived from $E.$ $coli$, and DNA endonuclease III, which is derived from $E.$ $coli$ Nth or the like. The former recognizes an abasic site in a DNA double helix and cleaves it off between 3' OH and 5' phosphoric acid. The latter enzyme forms a Schiff base with an abasic site of a deoxyribose, and 5' phosphoric acid is released from the ribose by beta-elimination in the Schiff base. When a base opposite the abasic site generated in a double-stranded DNA has been chemically modified, the amino acid residue at the active center of the endonuclease is expected to no longer bind to DNA.

CITATION LIST

Patent Literature

Patent Literature 1: WO2009/082020

Non-Patent Literature

Non-patent Literature 1: Cortellino S, et al. 2011 Cell 146, 67-79
Non-patent Literature 2: Biochemistry 1993, 32, 8276-8283
Non-patent Literature 3: BIOCHIMICA BIOPHYSICA ACTA 31 1959
Non-patent Literature 4: Chemical Research in Toxicology 2005, 18, 730-739

SUMMARY OF INVENTION

Technical Problem

An object of the present invention is to detect the presence of guanine opposite an abasic site generated in DNA and to detect which position in DNA the guanine is present at.

Solution to Problem

The present inventor conducted extensive research, and revealed that the problem can be solved by a method for detecting a guanine-abasic site by PCR amplification comprising the step of cleaving an abasic site generated in DNA and the step of chemically modifying a guanine base opposite the abasic site in order to detect the abasic site generated in DNA, or by using amplification of a guanine-abasic site-containing DNA fragment through PCR comprising the step of chemically modifying a guanine base opposite an abasic site generated in DNA without cleaving the abasic site and the step of purifying the biotinylated DNA on an avidin column.

The present invention provides the following method for detecting the presence or absence or the position of a guanine-abasic site in DNA, a method for quantifying the guanine-abasic sites, and kits therefor.

Item 1.

A method for detecting the presence or absence of a guanine-abasic site, the method being a process for detecting guanine opposite at least one abasic sites generated in a double-stranded DNA, comprising:

(1) step 1 of site-selectively cleaving at least one abasic sites in a double-stranded DNA using an enzyme;

(2) step 2 of modifying the amino group at position 2 of guanine opposite the abasic sites using a modifier; and (3) step 3 of performing polymerase chain reaction on the modified double-stranded DNA obtained by conducting step 1 and step 2, which serves as a template, to search for the presence or absence of an amplification product, the sequence of steps 1 and 2 being not limited to the order presented.

Item 2.

A method for quantifying a guanine-abasic site, the method being a process for detecting guanine opposite at least one abasic sites generated in a double-stranded DNA, comprising:

(1) step 1 of site-selectively cleaving at least one abasic sites in a double-stranded DNA using an enzyme;

(2) step 2 of modifying the amino group at position 2 of guanine opposite the abasic sites using a modifier; and (3) step 3 of performing real-time PCR on the modified double-stranded DNA obtained by conducting step 1 and step 2, which serves as a template, to quantify an amplification product, the sequence of steps 1 and 2 being not limited to the order presented.

Item 3.

A kit for detecting the presence or absence of a guanine-abasic site by performing polymerase chain reaction on a double-stranded DNA, which serves as a template, to search for the presence or absence of an amplification product, the kit comprising an endonuclease for site-selectively cleaving at least one abasic sites in a double-stranded DNA and glyoxal or a derivative of glyoxal for modifying the amino group at position 2 of guanine.

Item 4.

The kit according to item 3, wherein the endonuclease is E. coli-derived endonuclease III.

Item 5.

The kit according to item 3, wherein the derivative of glyoxal contains at least one aromatic ring or alkyl group.

Item 6.

The kit according to any one of items 3 to 5, further comprising a polar solvent for the glyoxal or the derivative of glyoxal.

Item 7.

A method for detecting the position of a guanine-abasic site, the method being a process for detecting guanine opposite at least one abasic sites generated in a double-stranded DNA, comprising:

(1) a step of biotinylating an unpaired guanine residue in a double-stranded DNA containing at least one abasic sites and the unpaired guanine;

(2) a step of purifying the biotinylated double-stranded DNA on an avidin column; and (3) a step of performing polymerase chain reaction on the purified biotinylated double-stranded DNA, which serves as a template, to search for the presence or absence of a mutation in a base sequence of an amplification product.

Item 8.

A kit for detecting the position of a guanine-abasic site, comprising a reagent for biotinylating an unpaired guanine residue in a double-stranded DNA containing at least one abasic site and the unpaired guanine and an avidin column.

Advantageous Effects of Invention

Endonucleases, which act on their substrate, abasic sites of DNA, are classified into two types: endonuclease IV and APEI nuclease, which are derived from E. coli, and DNA endonuclease III, which is derived from E. coli Nth or the like. The former recognizes an abasic site in a DNA double helix and cleaves it off between 3' OH and 5' phosphoric acid. The latter enzyme forms a Schiff base with an abasic site of a deoxyribose, and 5' phosphoric acid is released from the ribose by beta-elimination in the Schiff base. It has been newly found that when a base opposite an abasic site generated in a double-stranded DNA has been chemically modified, the amino acid residue tryptophan at the active center of the endonuclease is expected to no longer bind to the DNA, whereby the abasic site-containing chain serves as a PCR template; on the other hand, DNA endonuclease III derived from E. coli Nth or the like cleaves the abasic site-containing chain, making it impossible to perform amplification by PCR (Example 3). Therefore, whether a guanine-abasic site is present in a double-stranded DNA can be identified.

The present invention can accurately detect the presence or absence and the position of an abasic site in DNA in which cytosine has been eliminated from a GC base pair, thereby leaving guanine alone. The present invention can also quantify the abasic site.

DESCRIPTION OF EMBODIMENTS

The method for detecting the presence or absence of a guanine-abasic site according to the present invention comprises steps 1 to 3 described below.

The method for quantifying the guanine-abasic site according to the present invention comprises steps 1 and 2, which are the same as steps 1 and 2 for the method for detecting the presence or absence of a guanine-abasic site, and comprises step 3 of performing real-time PCR for quantification. Step 1 and step 2 can be performed without regard to the order. After step 1, step 2 may be performed, or after step 2, step 1 may be performed. After steps 1 and 2, step 3 is performed.

(1) Step 1

In step 1, at least one abasic sites in a double-stranded DNA is site-selectively cleaved. For this position selective cleavage, an enzyme is used. Examples of usable enzymes include endonucleases. Endonuclease III is preferable, and *E. coli*-derived endonuclease III is more preferable.

Step 1 can be performed by adding a suitable amount of an enzyme, such as an endonuclease (e.g., about 1 to 10,000 units per 10 pmol of DNA), to an aqueous solution containing target DNA for measurement and allowing a reaction to proceed at a temperature of about 37° C. for about 5 minutes to 10 hours.

(2) Step 2

The amino group at position 2 of guanine is modified with a modifier to end the base extension by PCR. Examples of modifiers include glyoxal and derivatives of glyoxal. Examples of the derivatives of glyoxal include compounds having at least one aromatic ring or alkyl group. The modifier used in the present invention is, for example, the compound represented by the following formula (I)

wherein $R^1$ and $R^2$ are the same or different, and represent hydrogen, alkyl, or optionally substituted aryl; $R^3$ and $R^4$ are the same or different, and represent alkoxy or optionally substituted aralkyloxy, or $R^3$ and $R^4$ represent carbonyl or alkylenedioxy together with the carbon atom to which $R^3$ and $R^4$ bond.

Examples of alkyl include linear, cyclic, or branched alkyl having 1 to 6 carbon atoms, and preferably 1 to 4 carbon atoms, such as methyl, ethyl, n-propyl, isopropyl, n-butyl, isobutyl, sec-butyl, tert-butyl, pentyl, hexyl, and cyclohexyl.

Examples of aryl include phenyl and naphthyl, with phenyl being preferable.

Examples of aralkyloxy include benzyloxy, phenethyloxy, and naphthylmethyloxy. Aralkyloxy (aryl alkyloxy) can be substituted in its aryl moiety.

Examples of alkoxy include linear or branched alkoxy having 1 to 6 carbon atoms, such as methoxy, ethoxy, n-propoxy, isopropoxy, n-butoxy, isobutoxy, sec-butoxy, tert-butoxy, pentyloxy, and hexyloxy.

Examples of alkylenedioxy include ethylenedioxy, propylenedioxy, and butylenedioxy.

Examples of substituents for aryl and aralkyloxy include alkoxy, such as OH, methoxy, ethoxy, n-propoxy, isopropoxy, n-butoxy, isobutoxy, sec-butoxy, tert-butoxy, pentyloxy, and hexyloxy; alkylthio, such as SH, methylthio, and ethylthio; monoalkylamino, such as amino, methylamino, and ethylamino; dialkylamino, such as dimethylamino and diethylamino; alkanoylamino, such as acetylamino; alkoxycarbonyl, such as COOH, methoxycarbonyl, ethoxycarbonyl, and butoxycarbonyl; arylcarbonyl, such as phenoxycarbonyl; aralkylcarbonyl, such as benzyloxycarbonyl; monoalkylcarbamoyl, such as carbamoyl ($CONH_2$), methylcarbamoyl, and ethylcarbamoyl; dialkyl carbamoyl, such as dimethyl carbamoyl and diethyl carbamoyl; CN; halogen atoms (F, Cl, Br, I); $NO_2$; and alkanoyl, such as acetyl. Aryl may have 1 to 5, preferably 1 to 3, of these substituents attached thereto.

Examples of preferable glyoxal derivatives include phenylglyoxal, trimethoxy phenylglyoxal, acetals thereof, and ketals thereof.

A modifier, such as glyoxal or a derivative of glyoxal, is added in an amount of about 0.01 μmol to 1,000 μmol per 6 pmol of DNA, and the mixture is allowed to react at a temperature from room temperature to about 40° C. for about 1 to 24 hours, thereby modifying the guanine residue in an abasic site (i.e., the site not forming a base pair). The reaction solvent used with the modifier may be water, and preferably a polar solvent, such as DMSO (dimethyl sulfoxide), DMF (dimethyl formamide), dimethylacetamide, dioxane, or N-methylpyrrolidone.

The guanine residue modified by a modifier, such as glyoxal or a derivative of glyoxal, cannot be involved in PCR, and PCR is ended at the site where the modified guanine residue is present.

(3) Step 3

In step 3, the polymerase chain reaction is performed on the double-stranded DNA modified by the modifier, which serves as a template, and whether an amplification product is present is examined. When a guanine residue opposite an abasic site (i.e., the site not forming a base pair) is modified by a modifier such as glyoxal or a derivative of glyoxal, PCR is ended at the modified guanine residue, leading to difficulty in obtaining a long PCR product. As the primer for PCR, those at the 5'- and 3'-sites flanking of the modified guanine residue are used. As PCR, real-time PCR is preferable. Performing real-time PCR enables the quantification of the guanine-abasic site. PCR is performed about 20 to 35 cycles, and preferably about 20 to 30 cycles.

The use of a primer flanking of a guanine-abasic site (G/AP site) for PCR enables the detection of the presence of and quantification of G/AP at a specific position. Examples of targets for detection of the G/AP site include promoters of genes involved in a variety of disorders, such as cancerization. A G/AP site generated in a promoter significantly affects the expression of the gene. In addition to promoter sites of genes, any site of DNA, such as coding regions of genes, can be the target for detection of a G/AP site.

The method according to the present invention can also analyze the total genomic DNA or part of the genomic DNA (e.g., specific chromosome). To do so, the genomic DNA is blunt-ended with a restriction enzyme, and a separate adaptor is attached to each side. Based on the sequence of the adaptors, PCR is then performed. This enables the determination of the total number of G/AP sites in the total genomic DNA or partial genomic DNA.

The method for detecting the position of a guanine-abasic site according to the present invention comprises the following 3 steps.

(1) Biotinylation Step

Biotinylation of an unpaired guanine residue in a double-stranded DNA containing the abasic sites and guanine (guanine residue of AP site) can be performed by allowing the double-stranded DNA to react with a biotinylation reagent.

Figure 3:
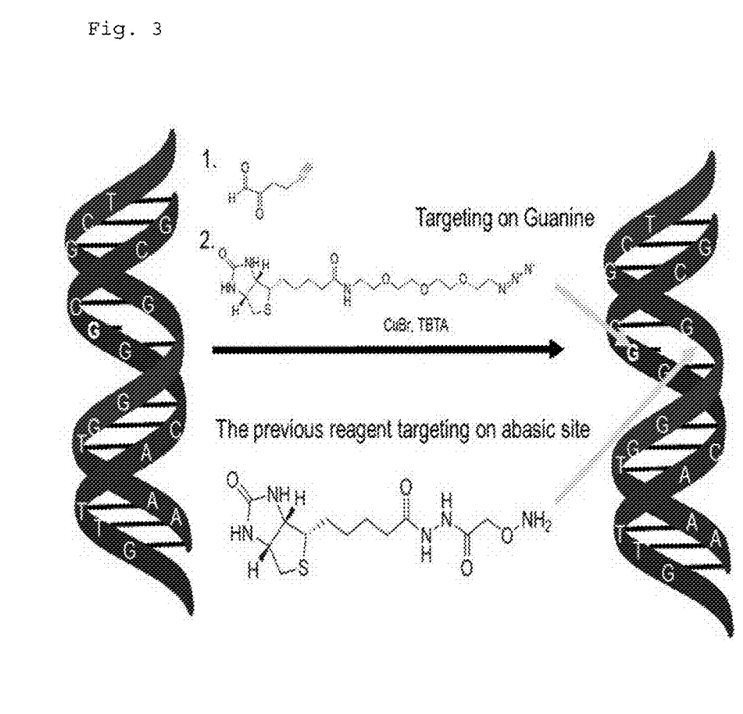
FIG. 3 shows biotinylation of a double-stranded DNA.

As a biotinylation reagent, a combination of the following reagents can be used: a reagent for introducing the acetylene group (—C≡C), such as 2-Oxohex-5-ynal as shown in FIG. 3 (Non-patent Literature 5, Chem Commun 2013, 49, 4012-4) and a reagent containing the biotin group and the azido group, such as Azide-PEO3-Biotin as shown in FIG. 3. Because 2-Oxohex-5-ynal contains the ketoaldehyde group and the acetylene group, 2-Oxohex-5-ynal can be reacted with guanine, and at the same time, guanine can biotinylated with acetylene by a click reaction. As a result, the removal of unmodified DNA has become possible. In addition, because the guanine base-containing chain of the double-stranded oligo DNA, which is purified on an avidin column, is completely masked by modification, it has been revealed for the first time that extension reaction by PCR causes a mutation of guanine to adenine (Example 6, FIG. 3). It has also been revealed that because the hydroxylamine biotinylation reagent disclosed in Patent Literature 1 masks the abasic site-containing chain, guanine in a fragment generated by PCR remains intact.

Guanine in an AP site is reacted with 2-Oxohex-5-ynal to introduce the acetylene group (—C≡C) into the guanine residue of the AP site. Subsequently, the resultant is reacted with a reagent containing the biotin group and the azido group to introduce the biotin group by a click reaction between the acetylene group and the azido group. As an acetylene group-introducing reagent, other reagents containing the acetylene group and the aldehyde group may be used. As a biotinylation group-introducing reagent, other reagents containing the azido group and the biotinylation group may be used.

The reaction for introducing the acetylene group can be favorably promoted by allowing the acetylene group-introducing reagent in a suitable amount (or an excess amount) as shown in Example 6 relative to the double-stranded DNA to react in a suitable solvent, such as a phosphoric acid buffer solution, at a temperature from room temperature to about 40° C. for 1 to 24 hours.

The reaction for introducing the biotin group (click reaction) can be favorably promoted by allowing a suitable amount (or an excess amount) of the biotin group-introducing reagent, CuBr and TBTA, as shown in Example 6, relative to the double-stranded DNA to which the acetylene group has been introduced to react in a suitable solvent, such as a TE buffer solution, at a temperature from room temperature to about 40° C. for 1 to 24 hours.

(2) Purification Step by Avidin Column

Purification of the biotinylated double-stranded DNA can be performed by using an avidin column in accordance with an ordinary technique. This purification step provides only a biotinylated double-stranded DNA, and performing PCR on this DNA makes it possible to detect the position of an AP site. When PCR is performed without this purification step, non-biotinylated double-stranded DNA is also amplified, thereby resulting in failure to detect the position of an AP site.

(3) Polymerase Chain Reaction (PCR)

Polymerase chain reaction using the purified biotinylated double-stranded DNA as a template can be performed in accordance with an ordinary technique. The obtained amplification product is sequenced, and examined for G→A mutation; this makes it possible to detect the position of an AP site. When amplification is performed using the abasic site-containing chain as a template, a double-stranded blunt end is once formed at the abasic sites, and adenine is inserted into the blunt end by Taq polymerase. This is why G is replaced with A in an AP site.

(4) Kit

The kit for detecting the presence or absence of a guanine-abasic site, or for quantifying the guanine-abasic site according to the present invention comprises the following components.

(i) An enzyme for site-selectively cleaving at least one abasic site in a double-stranded DNA, preferably an endonuclease, more preferably E. coli-derived endonuclease III
(ii) A modifier for selectively modifying a guanine residue that is not forming a base pair and opposite an abasic site, preferably glyoxal or a derivative of glyoxal, more preferably glyoxal or a derivative of glyoxal represented by formula (I).
(ii') A solvent for use in modification reaction (e.g., DMSO and DMF).
(iii) Components necessary for PCR, for example, a DNA polymerase such as Taq DNA polymerase, a PCR buffer, a dNTP mix, a primer mix, and a solvent (water).

The kit for detecting the position of a guanine-abasic site according to the present invention comprises the following components.

(i) A reagent for biotinylating an unpaired guanine residue at an AP site, for example, a combination of a reagent for introducing the acetylene group (—C≡C), such as 2-Oxohex-5-ynal, and a reagent for introducing the biotin group by the click reaction, such as Azide-PEO3-Biotin.
(ii) An avidin column
(iii) Components necessary for PCR, for example, a DNA polymerase such as Taq DNA Polymerase, a PCR buffer, a dNTP mix, a primer mix, and a solvent (water).

EXAMPLES

The following describes the present invention based on Examples. Needless to say, however, the present invention is not limited to the Examples.

Example 1

A double-stranded oligo DNA containing a guanine-abasic site for use in the present invention was prepared in accordance with the following procedure. Artificially prepared 100-mer oligo DNA (20131226U) containing dU was treated with uracil DNA glycosylase (UDG), and hybridized with artificially prepared 100-mer oligo DNA (20131226G). 100-mer oligo DNA (20131226U) represents 5'TGA CTT GCC ACC TAT AGA CAG CCC TTG CTC TCC TGC AGA GTT TGG CAA TGA CTC UGG TCA CTG CAT CTG TGG GAC CTG GCT CAG TCT GCC AAC TTC ACT G3' (SEQ ID NO:1), whereas DNA (20131226G) represents 5'CAG TGA AGT TGG CAG ACT GAG CCA GGT CCC ACA GAT GCA GTG ACC GGA GTC ATT GCC AAA CTC TGC AGG AGA GCA AGG GCT GTC TAT AGG TGG CAA GTC A 3' (SEQ ID NO:2). 100 pmol of 100-mer oligo DNA (20131226U) was dissolved in a 1×UDG buffer (600 µl), and heated at 90° C. for 1 minute, followed by cooling with ice. UDG (30 units, 6 µl) was then added thereto, and the mixture was allowed to react at 37° C. for 1 hour. After the reaction, an equimolar amount of 100-mer oligo DNA (20131226G), which is the complementary strand, was added thereto, and the mixture was heated at 90° C. for 10 minutes. The heated mixture was then allowed to stand to cool to room temperature. The double-stranded DNA in the reaction solution was adsorbed on silica gel included in a Nucleospin Gel and PCR Clean up kit, and then the double-stranded oligo DNA containing a guanine-abasic site was eluted with a 0.5 M phosphoric acid buffer solution (pH 7.4) or a 5 mM Tris-HCl buffer solution (pH 8.5).

Example 2

Figure 4:
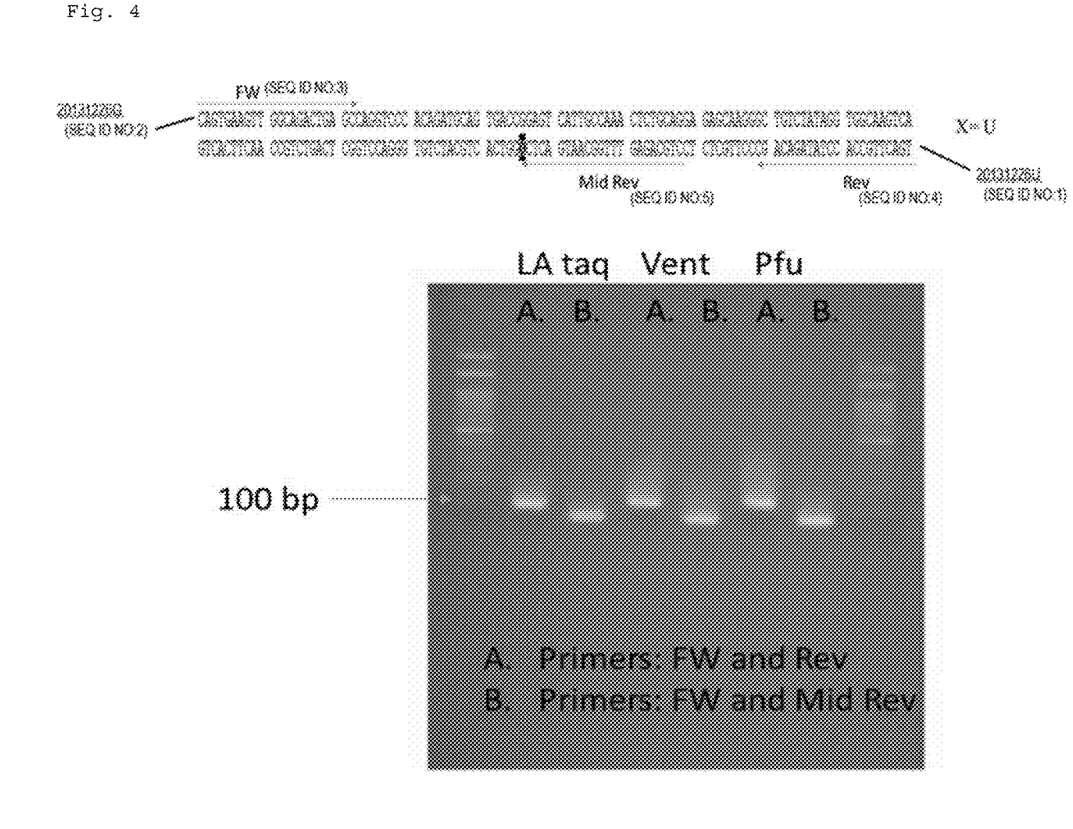
FIG. 4 shows the results of electrophoresis in Example 2.

The double-stranded oligo DNA (10 µl, 6 pmol) eluted with a 0.5 M phosphoric acid buffer solution (pH 7.4) of Example 1 was mixed with 10 μl of a 0.3 M solution of glyoxal in DMSO, and the mixture was incubated at 37° C. for 12 hours. After the reaction, the resultant was placed on an NAP-5 column, and eluted with a 10 mM TE buffer solution. The oligo DNA fragment was amplified by PCR using LA Taq DNA polymerase, Vent (*Thermococcus litoralis*) DNA polymerase, and *Pyrococcus furiosus* Taq. PCR was performed in the following manner; after a pre-reaction at 95° C. for 1 minute, PCR at 95° C. for 30 seconds, PCR at 55° C. for 30 seconds, and PCR at 72° C. for 30 seconds was repeated 30 cycles. The following primers were used: FW: 5'CAG TGA AGT TGG CAG ACT GAG C3' (SEQ ID NO:3), Rev: 5'CTG ACT TGC CAC CTA TAG ACA GC3' (SEQ ID NO:4), and MidRev: 5'CTG CAG AGT TTG GCA ATG ACT CC3' (SEQ ID NO:5) (FIG. 4). The results revealed that subjecting the double-stranded oligo DNA containing guanine opposite an abasic site to a reaction with glyoxal does not affect the amplification by DNA polymerase chain reaction at all.

Figure 5:
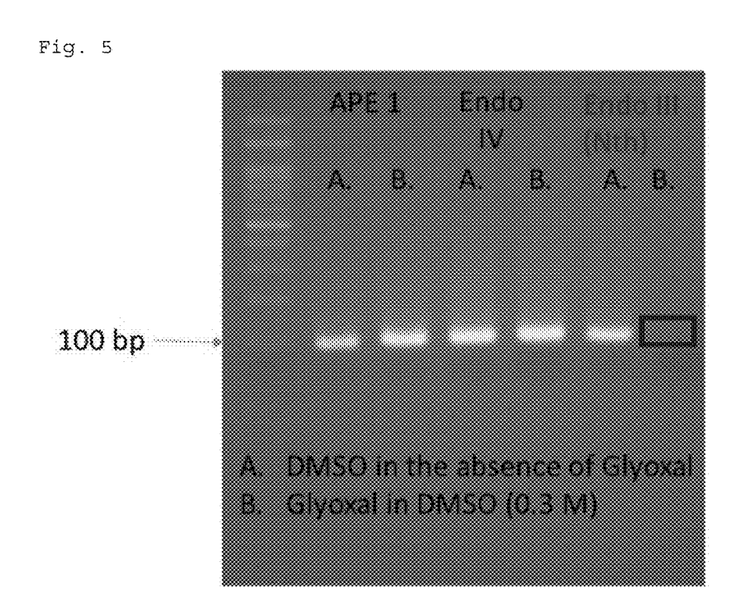
FIG. 5 shows the results of electrophoresis in Example 3.

Example 3: Reaction with Glyoxal after Endonuclease Treatment 20 pmol of the double-stranded oligo DNA solution eluted with a 5 mM Tris-HCl buffer solution (pH 8.5) in Example 1 was reacted with 60 units of APE1 or endonuclease IV at 37° C. for 1 hour. The double-stranded oligo DNA in the reaction solution was adsorbed on silica gel included in a Nucleospin Gel and PCR Clean up kit, and eluted with a 0.5 M phosphoric acid buffer solution (pH 7.4). When endonuclease III was used, 300 units of endonuclease III was directly added to a UDG reaction solution containing 100 pmol of the oligo DNA of Example 1, and the mixture was subjected to a reaction at 37° C. for 1 hour. The reaction solution was then purified with the Nucleospin Gel and PCR Clean up kit, and eluted with a 0.5 M phosphoric acid buffer solution (pH 7.4). The respective double-stranded oligo DNAs (10 μl, 6 pmol) were mixed with 10 μl of a 0.3 M solution of glyoxal in DMSO, and the mixtures were individually incubated at 37° C. for 12 hours. After the reaction, the resultants were placed on an NAP-5 column, and eluted with a 10 mM TE buffer solution. The oligo DNA fragments were then amplified by PCR using LA Taq DNA polymerase. As a result, only in the case of the treatment with endonuclease III and glyoxal, the amplification by a DNA polymerase was ended (FIG. 5).

Example 4

Figure 6:
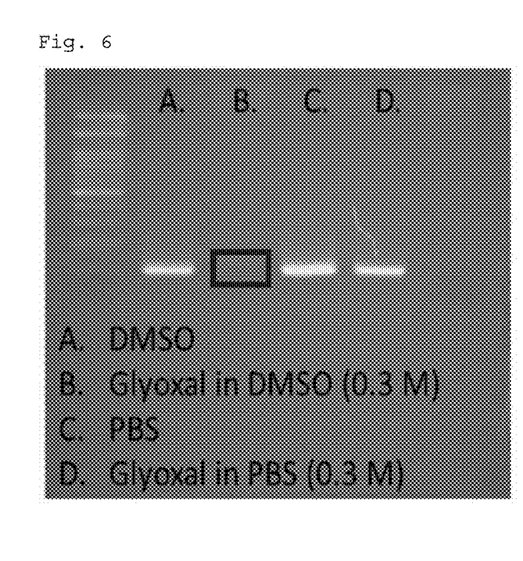
FIG. 6 shows the results of electrophoresis in Example 4.

The double-stranded oligo DNA (10 μl, 6 pmol) cleaved by endonuclease III in Example 3 was mixed with 10 μl of a 0.3 M solution of glyoxal in DMSO or a phosphoric acid buffer solution, and the mixture was incubated at 37° C. for 12 hours. After the reaction, the resultant was placed on an NAP-5 column, and eluted with 10 mM of a TE buffer solution. PCR using LA Taq DNA polymerase was performed on the oligo DNA fragments to confirm the amplification. As shown in FIG. 6, the DMSO solution yielded a good result.

Example 5

The double-stranded oligo DNA (10 μl, 6 pmol) cleaved by endonuclease III in Example 3 was mixed with 10 μl of a 0.3 M solution of glyoxal, phenylglyoxal, or trimethoxy-phenylglyoxal in DMSO, and the respective mixtures were incubated at 37° C. for 12 hours. After the reaction, the resultants were placed on an NAP-5 column, and eluted with a 10 mM TE buffer solution. PCR using LA Taq DNA polymerase was performed on the oligo DNA fragments for 20 or 30 cycles to confirm the amplification.

Figure 7:
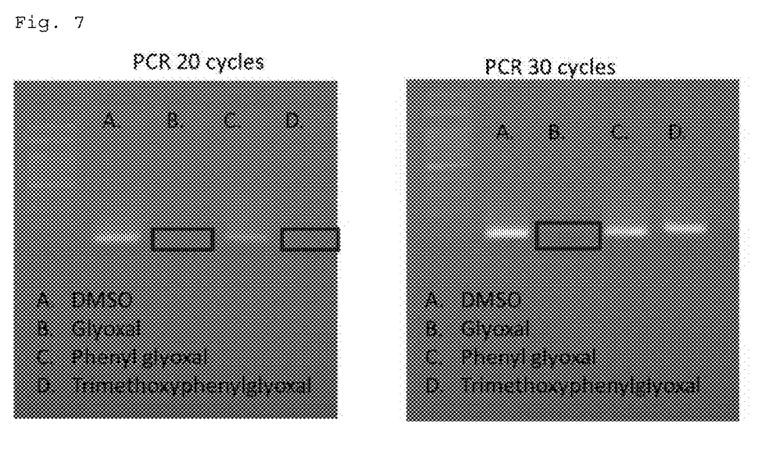
FIG. 7 shows the results of electrophoresis in Example 5.

As shown in FIG. 7, the results revealed that the reactivity of glyoxal was the highest.

Example 6

Figure 8:
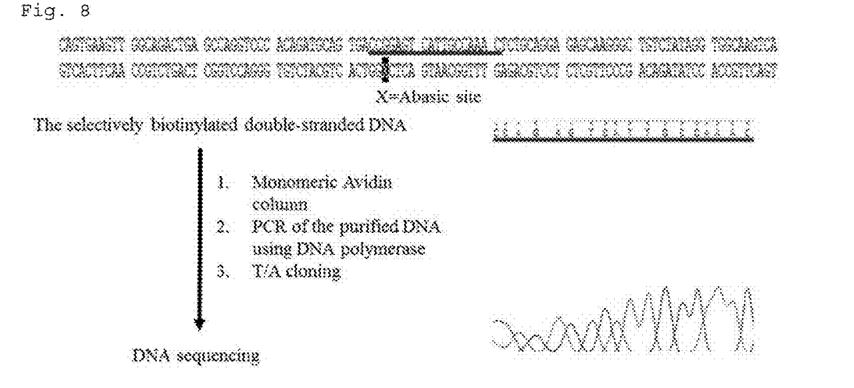
FIG. 8 shows the results of electrophoresis in Example 6.

500 ng of double-stranded oligo DNA containing a guanine-abasic site prepared in accordance with the procedure described in Example 1 was mixed with a phosphoric acid buffer solution and a solution of 2-Oxohex-5-ynal in DMSO (0.3 M) disclosed in Non-patent Literature 5. The mixture was incubated at 37° C. for 12 hours. After the reaction, the resultant was placed on a G-50 microcolumn, and eluted with 0.05 ml of a 10 mM TE buffer solution. The collected solution was mixed with 0.01 ml of a 0.1-M CuBr solution, 0.02 ml of a 0.1-M TBTA solution, and 0.02 ml of a 0.002 M Azido-PEO3-Biotin (all products produced by Jena Bioscience), and the mixture was incubated at 37° C. for 2 hours. After the reaction product was centrifuged, the resultant was placed on an NAP-5 column, and eluted with 0.5 ml of a 10 mM TE buffer solution. Subsequently, the eluate was purified over 0.5 ml of an avidin column (Pierce), and amplified by PCR using Taq DNA polymerase. In addition, the PCR product was cloned into pGEM T-vector (Promega), and the base sequence of the DNA was determined. The results revealed that guanine facing an abasic site mutated into adenine (FIG. 8).

Example 7

Figure 9:
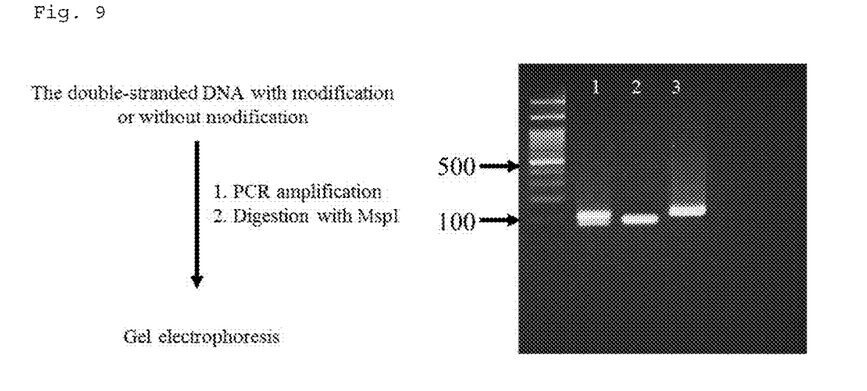
FIG. 9 shows the results of electrophoresis in Example 7.

The sequence of the PCR product was also examined using a restriction enzyme. As shown in Example 6, after modification with 2-Oxohex-5-ynal, a reaction using a restriction enzyme MspI, which recognizes the CCGG sequence, was allowed to proceed in an NEB buffer 4 solution, and then electrophoresis was performed in 2% agarose gel. The results revealed that the PCR product (100 bp) was not cleaved (electrophoresis 3). The results also support the mutation of guanine into adenine. Also, 500 ng of double-stranded oligo DNA containing a guanine-abasic site was mixed with a commercially available hydroxy amino biotin compound, and the mixture was incubated in a phosphoric acid buffer solution at 37° C. for 2 hours. The resultant was placed on an NAP-5 column, and eluted with 0.5 ml of a 10 mM TE buffer solution, followed by purification on an avidin column. PCR using Taq DNA polymerase was performed on the purified biotinylated double-stranded oligo DNA as a template under the same conditions as described above to amplify the DNA fragment. The amplified fragment was purified with a Nucleospin Gel and PCR Clean up kit, and then diluted with an NEB buffer 4 solution, followed by a reaction with a restriction enzyme MspI, which recognizes the CCGG sequence. The results of electrophoresis performed in a 2% agarose gel revealed that the double-stranded DNA was completely cleaved (electrophoresis 2). In addition, PCR using a DNA polymerase was performed on 1 ng of non-biotinylated double-stranded oligo DNA containing a guanine-abasic site as a template under the same conditions as described above to amplify the DNA fragment. The resultant was purified with a Nucleospin Gel and PCR Clean up kit, and reacted with a restriction enzyme MspI, which recognizes the CCGG sequence, followed by electrophoresis in a 2% agarose gel. As a result, a band of a double-stranded DNA was found (electrophoresis 1). This is because both the abasic site-containing chain and the chain containing the unpaired guanine served as a template for PCR (FIG. 9).

The invention claimed is:

1. A method for detecting the position of a guanine-abasic site generated in a double-stranded DNA, comprising:
   (1) biotinylating an unpaired guanine residue in a double-stranded DNA containing at least one abasic site and the unpaired guanine;
   (2) purifying the biotinylated double-stranded DNA on an avidin column;
   (3) performing polymerase chain reaction on the purified biotinylated double-stranded DNA, which serves as a template and obtaining an amplification product;
   (4) searching for a mutation from guanine to adenine in a base sequence of the amplification product; and
   (5) detecting the position of the mutation from guanine to adenine as the position of the guanine-abasic site.

2. The method according to claim 1, wherein biotinylating the unpaired guanine residue in step (1) is performed by
   (i) introducing an acetylene group into the guanine residue of the guanine-abasic site, and
   (ii) reacting the resultant with a reagent containing a biotin group and an azido group.

3. The method according to claim 2, wherein the reagent for introducing an acetylene group is 2-Oxohex-5-ynal.

4. The method according to claim 2, wherein the reagent containing a biotin group and an azido group is Azido-PEO3-Biotin.

5. The method according to claim 1, wherein non-biotinylated double-stranded DNA is removed in step (2).

6. The method according to claim 1, wherein polymerase chain reaction in step (3) is performed using Taq DNA polymerase.

7. The method according to claim 1 wherein searching for a mutation from guanine to adenine in step (4) is performed by DNA sequencing.

* * * * *

UNITED STATES PATENT AND TRADEMARK OFFICE
CERTIFICATE OF CORRECTION

PATENT NO. : 10,370,703 B2  
APPLICATION NO. : 15/126178  
DATED : August 6, 2019  
INVENTOR(S) : Chun Wu Page 1 of 1

It is certified that error appears in the above-identified patent and that said Letters Patent is hereby corrected as shown below:

On the Title Page

Item (87): "PCT Pub. No.: WO2016/136999" should read "PCT Pub. No.: WO2015/136999"

Signed and Sealed this  
Twenty-sixth Day of November, 2019

Andrei Iancu  
*Director of the United States Patent and Trademark Office*